United States Patent
Dakka et al.

(10) Patent No.: US 9,758,447 B2
(45) Date of Patent: Sep. 12, 2017

(54) ACTIVATION OF DEHYDROGENATION CATALYSTS

(71) Applicant: ExxonMobil Chemical Patents Inc., Baytown, TX (US)

(72) Inventors: Jihad M. Dakka, Whitehouse Station, NJ (US); Lorenzo C. DeCaul, Langhorne, PA (US); Gregory J. De Martin, Flemington, NJ (US); Michael Salciccioli, Houston, TX (US); Neeraj Sangar, League City, TX (US); Aaron B. Pavlish, Humble, TX (US); Ali A. Kheir, Sugar Land, TX (US); Gary D. Mohr, Sunset, SC (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 222 days.

(21) Appl. No.: 14/878,753

(22) Filed: Oct. 8, 2015

(65) Prior Publication Data

US 2016/0115095 A1    Apr. 28, 2016

Related U.S. Application Data

(60) Provisional application No. 62/068,144, filed on Oct. 24, 2014.

(51) Int. Cl.
*C07C 5/367*    (2006.01)
*C07C 5/32*    (2006.01)
(Continued)

(52) U.S. Cl.
CPC .............. *C07C 5/367* (2013.01); *B01J 23/626* (2013.01); *B01J 29/7476* (2013.01);
(Continued)

(58) Field of Classification Search
CPC ........ C07C 5/367; C07C 2/74; C07C 2601/14; C07C 2523/14; C07C 2523/42;
(Continued)

(56) References Cited

U.S. PATENT DOCUMENTS 2,520,084 A    8/1950    Dazzi
2,634,248 A    4/1953    Dazzi
(Continued)

FOREIGN PATENT DOCUMENTS

JP    03-106833 A    5/1991
JP    07-173086 A    7/1995
(Continued)

OTHER PUBLICATIONS

U.S. Appl. No. 61/040,480, filed Mar. 28, 2008, Godwin.
(Continued)

*Primary Examiner* — Brian McCaig
*Assistant Examiner* — Jason Chong

(57) ABSTRACT

In a process for dehydrogenating cyclohexylbenzene and/or alkyl-substituted cyclohexylbenzene compounds, a dehydrogenation catalyst comprising at least one Group 10 metal compound on a support is heated in the presence of hydrogen from a first temperature from 0° C. to 200° C. to a second, higher temperature from 60° C. to 500° C. at a ramp rate no more than 100° C./hour. The dehydrogenation catalyst is contacted with hydrogen at the second temperature for a time from 3 to 300 hours to produce an activated dehydrogenation catalyst. A feed comprising cyclohexylbenzene and/or an alkyl-substituted cyclohexylbenzene compound is then contacted with hydrogen in the presence of the activated dehydrogenation catalyst under conditions effective to produce a dehydrogenation reaction product comprising biphenyl and/or an alkyl-substituted biphenyl compound.

25 Claims, 2 Drawing Sheets

(51) Int. Cl.
*C07C 2/74* (2006.01)
*B01J 37/18* (2006.01)
*B01J 37/02* (2006.01)
*B01J 23/62* (2006.01)
*B01J 29/74* (2006.01)

(52) U.S. Cl.
CPC ........... *B01J 37/0205* (2013.01); *B01J 37/18* (2013.01); *C07C 2/74* (2013.01); *B01J 2229/186* (2013.01); *B01J 2229/42* (2013.01); *C07C 2521/04* (2013.01); *C07C 2521/08* (2013.01); *C07C 2523/14* (2013.01); *C07C 2523/42* (2013.01); *C07C 2523/62* (2013.01); *C07C 2529/74* (2013.01); *C07C 2601/14* (2017.05)

(58) Field of Classification Search
CPC ........... C07C 2521/04; C07C 2529/74; C07C 2521/08; B01J 23/626; B01J 37/0205; B01J 29/7476; B01J 37/18; B01J 2229/42; B01J 2229/186
See application file for complete search history.

(56) References Cited

U.S. PATENT DOCUMENTS

| | | | |
|---|---|---|---|
| 2,976,266 | A | 3/1961 | Lytton et al. |
| 3,296,065 | A | 1/1967 | O'Brien et al. |
| 3,842,040 | A | 10/1974 | Browne et al. |
| 3,842,041 | A | 10/1974 | Browne et al. |
| 3,928,481 | A | 12/1975 | Suggitt |
| 3,928,484 | A | 12/1975 | Suggitt |
| 3,962,362 | A | 6/1976 | Suggitt |
| 4,123,470 | A | 10/1978 | Murtha |
| 4,218,572 | A | 8/1980 | Dolhyj et al. |
| 4,263,457 | A | 4/1981 | Takeda et al. |
| 4,294,976 | A | 10/1981 | Itatani et al. |
| 4,463,207 | A | 7/1984 | Johnson |
| 4,959,450 | A | 9/1990 | Morris et al. |
| 5,001,296 | A | 3/1991 | Howley et al. |
| 5,138,022 | A | 8/1992 | Mang et al. |
| 6,037,513 | A | 3/2000 | Chang et al. |
| 6,103,919 | A | 8/2000 | Schiraldi et al. |
| 6,274,756 | B1 | 8/2001 | Caers et al. |
| 6,355,711 | B1 | 3/2002 | Godwin et al. |
| 6,433,236 | B1 | 8/2002 | Schiraldi et al. |
| 6,482,972 | B1 | 11/2002 | Bahrmann et al. |
| 6,730,625 | B1 | 5/2004 | Chang et al. |
| 6,740,254 | B2 | 5/2004 | Zhou et al. |
| 6,777,514 | B2 | 8/2004 | Patil et al. |
| 7,297,738 | B2 | 11/2007 | Gosse et al. |
| 7,579,511 | B1 | 8/2009 | Dakka et al. |
| 8,829,093 | B2 | 9/2014 | Dakka et al. |
| 2005/0137437 | A1 | 6/2005 | Soloveichik et al. |
| 2005/0215433 | A1 | 9/2005 | Benitez et al. |
| 2006/0247461 | A1 | 11/2006 | Schlosberg et al. |
| 2008/0242895 | A1 | 10/2008 | Godwin et al. |
| 2009/0299111 | A1 | 12/2009 | Kanbara et al. |
| 2010/0159177 | A1 | 6/2010 | Dakka et al. |
| 2011/0151162 | A1 | 6/2011 | Dakka et al. |
| 2011/0184105 | A1 | 7/2011 | Dakka et al. |
| 2011/0215433 | A1 | 9/2011 | Kokubum |
| 2012/0108726 | A1 | 5/2012 | Godwin et al. |
| 2012/0108874 | A1 | 5/2012 | Gralla et al. |
| 2012/0283494 | A1 | 11/2012 | Smith et al. |
| 2014/0066663 | A1 | 3/2014 | Dakka et al. |
| 2014/0212666 | A1 | 7/2014 | Dakka et al. |
| 2014/0272626 | A1 | 9/2014 | Berlowitz et al. |
| 2014/0275605 | A1 | 9/2014 | Dakka et al. |
| 2014/0275606 | A1 | 9/2014 | Bai et al. |
| 2014/0275607 | A1 | 9/2014 | Dakka et al. |
| 2014/0275609 | A1 | 9/2014 | Dakka et al. |
| 2014/0315021 | A1 | 10/2014 | Naert et al. |
| 2014/0316155 | A1 | 10/2014 | Dakka et al. |
| 2014/0323782 | A1 | 10/2014 | Chen et al. |
| 2014/0378697 | A1 | 12/2014 | de Smit et al. |
| 2015/0080545 | A1 | 3/2015 | Dakka et al. |
| 2015/0080546 | A1 | 3/2015 | Dakka et al. |

FOREIGN PATENT DOCUMENTS

| | | |
|---|---|---|
| JP | 08-020548 A | 1/1996 |
| JP | 08-099914 | 4/1996 |
| SU | 412182 | 1/1974 |
| WO | WO 99/32427 | 7/1999 |
| WO | WO 03/029339 | 4/2003 |
| WO | WO 2004/046078 | 6/2004 |
| WO | WO 2007/013469 | 2/2007 |
| WO | WO 2010/138248 | 12/2010 |
| WO | WO 2011/096989 | 8/2011 |
| WO | WO 2011/096993 | 8/2011 |
| WO | WO 2012/082407 | 6/2012 |
| WO | WO 2014/159094 | 10/2014 |
| WO | WO 2014/159104 | 10/2014 |

OTHER PUBLICATIONS

U.S. Appl. No. 61/203,626, filed Dec. 24, 2008, Dakka et al.
U.S. Appl. No. 61/577,900, filed Dec. 20, 2011, Dakka et al.
U.S. Appl. No. 61/781,109, filed Mar. 14, 2013, Dakka et al.
U.S. Appl. No. 61/781,116, filed Mar. 14, 2014, Bai et al.
U.S. Appl. No. 61/781,129, filed Mar. 14, 2014, Dakka et al.
U.S. Appl. No. 61/781,137, filed Mar. 14, 2014, Dakka et al.
U.S. Appl. No. 61/781,728, filed Mar. 14, 2014, Dakka et al.
U.S. Appl. No. 62/012,024, filed Jun. 13, 2014, Salciccioli et al.
U.S. Appl. No. 62/012,037, filed Jun. 13, 2014, Dakka et al.
U.S. Appl. No. 62/026,889, filed Jan. 27, 2015, Dakka et al.
U.S. Appl. No. 62/068,144, filed Oct. 24, 2014, Dakka et al.
U.S. Appl. No. 62/094,218, filed Dec. 19, 2014, Salciccioli et al.
U.S. Appl. No. 62/137,996, filed Mar. 25, 2015, Salciccioli et al.
U.S. Appl. No. 62/138,179, filed Mar. 25, 2015, Evans et al.
U.S. Appl. No. 62/140,723, filed Mar. 31, 2015, Salciccioli et al.
U.S. Appl. No. 13/316,745, filed Dec. 12, 2011, Patil et al.
U.S. Appl. No. 14/164,889, filed Jan. 27, 2014, Dakka et al.
U.S. Appl. No. 14/201,173, filed Mar. 7, 2014, Dakka et al.
U.S. Appl. No. 14/201,224, filed Mar. 7, 2014, Dakka et al.
U.S. Appl. No. 14/201,226, filed Mar. 7, 2014, Bai et al.
U.S. Appl. No. 14/201,284, filed Mar. 7, 2014, Dakka et al.
U.S. Appl. No. 14/201,287, filed Mar. 7, 2014, Dakka et al.
U.S. Appl. No. 14,480,363, filed Sep. 8, 2014, Dakka et al.
U.S. Appl. No. 14/486,945, filed Sep. 15, 2014, Dobin et al.
U.S. Appl. No. 14/516,239, filed Oct. 16, 2014, Dakka et al.
U.S. Appl. No. 14/527,480, filed Oct. 29, 2014, Patil et al.
Bandyopadhyay et al., "*Transalkylation of cumene with toluene over zeolite Beta*," Applied Catalysis A: General, 1996, vol. 135(2), pp. 249-259.
Bandyopadhyay et al., "*Transalkylation reaction—An alternative route to produce industrially important intermediates such as cymene*," Catalysis Today, 1998, vol. 44, pp. 245-252.
Borodina et al., "Hydroalkylation of Benzene and Ethylbenzene over Metal-Containing Zeolite Catalysts," Petroleum Chemistry, 2009, vol. 49(1), pp. 66-73.
Clary et al., "*A Green, One-Pot Route to the Biphenyldicarboxylic Acids: Useful Intermediates in Polymer Synthesis*," International Journal of Organic Chemistry, Jun. 2013, vol. 3(2), pp. 143-147.
Ennis et al., "*Multikilogram-Scale Synthesis of a Biphenyl Carboxylic Acid Derivative Using a Pd/C-Mediated Suzuki Coupling Approach*," Organic Process Research & Development, 1999, vol. 3(4), pp. 248-252.
Godwin, et al., "*Plasticizers*," Applied Polymer Science: 21st Century, Elsevier, 2000, pp. 157-175.
Guo, et al., "*Reactivity of 4,4'-Dimethylbiphenyl with Methanol over modified HZSM-5 Catalysts*," PrePrints—American Chemical Society, Division of Petroleum Chemistry, 2003, vol. 48(4), pp. 280-282.
Hoefnagel et al., "Selective alkylation of methylbenzenes with cyclohexene catalyzed by solid acids," Catalysis Letters, vol. 85, No. 1-2, 2003, pp. 7-11.

(56) References Cited

OTHER PUBLICATIONS

Izard, "Effect of Chemical Structure on Physical Properties of Isomeric Polyesters," Journal of Polymer Science, 1952, vol. 9(1), 35-39.

Khromov et al., "*Catalytic Conversion of 1,1'-Dimethyldicyclohexyl and 1-Methyl-1-Phenyl-Cyclohexane on Platinum Catalysts at Elevated Hydrogen Pressures and Temperatures*," Vestnik Moskovskogo Universiteta, Seriya 2: Khimiya (1965), 20(1), 51-5, (English AbstractOnly).

Krigbaum et al., "Aromatic Polyesters Forming Thermotropic Smectic Mesophases," Journal of Polymer Science, Part C, Polymer Letters Edition, 1982, vol. 20(2), pp. 109-115.

Kulev et al., "*Esters of diphenic acid and their plasticizing properties*," Izvestiya Tomskogo Politekhnicheskogo Instituta, 1961, vol. 111 (Abstract).

Lagidze et al., "*Analysis of Substances Produced by Reaction Between Aluminum Chloride and Diphenyl in Dearomatized Ligroin*," V.I. Leni-n Georgian Polytechnic Institute (1968), No. 2 (122), pp. 36-44. (English Translation).

Lu et al., "Selective Hydrogenation of Single Benzene Ring in Biphenyl Catalyzed by Skeletal Ni," ChemCatChem., 2009, vol. 1(3), pp. 369-371.

Mavrodinova et al., "Transalkylation of toluene with cumene over zeolites Y dealuminated in solid-state, Part I. Effect of the alteration of Broensted acidity," Applied Catalysis A: General, 2003, vol. 248, pp. 181-196.

Mavrodinova et al., "Transalkylation of toluene with cumene over zeolites Y dealuminated in solid-state Part II. Effect of the introduced Lewis acid sites," Applied Catalysis A: General, 2003, vol. 248, p. 197-209.

Meurisse et al., "Polymers with Mesogenic Elements and Flexible Spacers in the Main Chain: Aromatic-Aliphatic Polyesters," British Polymer Journal, 1981, vol. 13(2), pp. 55-63.

Mukhopadhyay et al., "*Tandem One-Pot Palladium-Catalyzed Reductive and Oxidative Coupling of Benzene and Chlorobenzene*," Journal of Organic Chemistry, 2000, vol. 65(10), pp. 3107-3110.

Roux et al., "Critically Evaluated Thermochemical Properties of Polycyclic Aromatic Hydrocarbons," Journal of Physical and Chemical Reference Data, 2008, vol. 37(4), pp. 1855-1996.

Sherman et al., "Dimethylbiphenyls from toluene," American Chemical Society, Chemical Innovation, 2000, pp. 25-30.

Shioda et al., "*Synthesis of dialkyl diphenates and their properties*," Yuki Gosei Kagaku Kyokaishi 1959, 17. (Abstract).

Sinfelt, "The turnover frequency of methylcyclohexane dehydrogenation to toluene on a Pt reforming catalyst," Journal of Molecular Catalysis A: Chemical, 2000, vol. 163, pp. 123-128.

Sinfelt et al., "Kinetics of Methylcyclohexane Dehydrogenation Over Pt—$Al_2O_3$," Journal of Physical Chemistry, 1960, vol. 64(10), 1559-1562.

Singh, et. al, "*Studies on Isomer Distribution in the Products Obtained by Friedelcrafts Alkylation of Toluene with Cyclic Electrophiles*," National Academy Science Letters, 1983, vol. 6(10), pp. 321-325.

Zhang, et al., "Automation of Fluorous Solid-Phase Extraction for Parallel Synthesis," J. Comb. Chem, 2006, vol. 8, pp. 890-896.

Depboylu, Can Okan, "An investigation of catalyst preparation conditions and promoter loading (Sn) effects on activity and selectivity of Pt catalyists in citral hydrogenation," Izmir Institute of Technology, Master Thesis, 2010, pp. 1-59.

ACTIVATION OF DEHYDROGENATION CATALYSTS

PRIORITY

This invention claims priority to and the benefit of U.S. Ser.No. 62/068,144, filed Oct. 24, 2014.

FIELD OF THE INVENTION

This disclosure relates to activation of dehydrogenation catalysts useful in the production of methylbiphenyl compounds.

BACKGROUND OF THE INVENTION

Methylbiphenyl compounds are useful intermediates in the production of a variety of commercially valuable products, including polyesters and plasticizers for PVC and other polymer compositions. For example, they can be converted to an ester plasticizer by a process comprising oxidation to produce the corresponding mono- or dicarboxylic acid followed by esterification of the acid function with a long chain alcohol. In addition, diphenyl-4,4'-dicarboxylic acid, optionally together with diphenyl-3,4'-dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

As disclosed in our co-pending U.S. patent application Ser. Nos. 14/201,287 and 14/201,224, both filed Mar. 7, 2014 and incorporated herein by reference, dimethylbiphenyl compounds may be produced by hydroalkylation of toluene followed by dehydrogenation of the resulting (methylcyclohexyl)toluene (MCHT). An alternative route via benzene is described in our co-pending U.S. patent application Ser. No. 14/164,889, filed Jan. 27, 2014 and also incorporated herein by reference. In this alternative route, the benzene is initially hydroalkylated to cyclohexylbenzene (CHB), which is then dehydrogenated to biphenyl. The biphenyl is subsequently alkylated with methanol to produce the desired methylbiphenyl compounds.

One problem with both of these routes for producing methylbiphenyl compounds is that the catalyst employed in the dehydrogenation step tends to undergo rapid deactivation. There is therefore interest in developing an improved dehydrogenation catalyst that exhibits enhanced stability when employed in the dehydrogenation of MCHT and and/or CHB.

SUMMARY OF THE INVENTION

According to the present invention, it has now surprisingly been found that the stability of MCHT and CHB dehydrogenation catalysts can be improved by controlling certain conditions, such as the temperature ramp rate, the final temperature and the hydrogen feed rate, used to activate the catalyst. In addition, further improvements in catalyst stability can be achieved by controlling the dehydrogenation conditions and/or by reducing or eliminating the amount of heavy compounds, particularly, dicyclohexylbenzene compounds, in the dehydrogenation feed.

In one aspect, the invention resides in a process for dehydrogenating cyclohexylbenzene and/or alkyl-substituted cyclohexylbenzene compounds, the process comprising:

(a) providing a dehydrogenation catalyst comprising at least one Group 10 metal compound on a support;

(b) heating the dehydrogenation catalyst in the presence of hydrogen from a first temperature from 0° C. to 200° C. to a second, higher temperature from 60° C. to 500° C. at a ramp rate no more than 100° C./hour;

(c) contacting the dehydrogenation catalyst with hydrogen at the second temperature for a time from 3 to 300 hours to produce an activated dehydrogenation catalyst; and (d) contacting a feed comprising cyclohexylbenzene and/or an alkyl-substituted cyclohexylbenzene compound with hydrogen in the presence of the activated dehydrogenation catalyst under conditions effective to produce a dehydrogenation reaction product comprising biphenyl and/or an alkyl-substituted biphenyl compound.

DETAILED DESCRIPTION OF THE EMBODIMENTS

Figure 1:
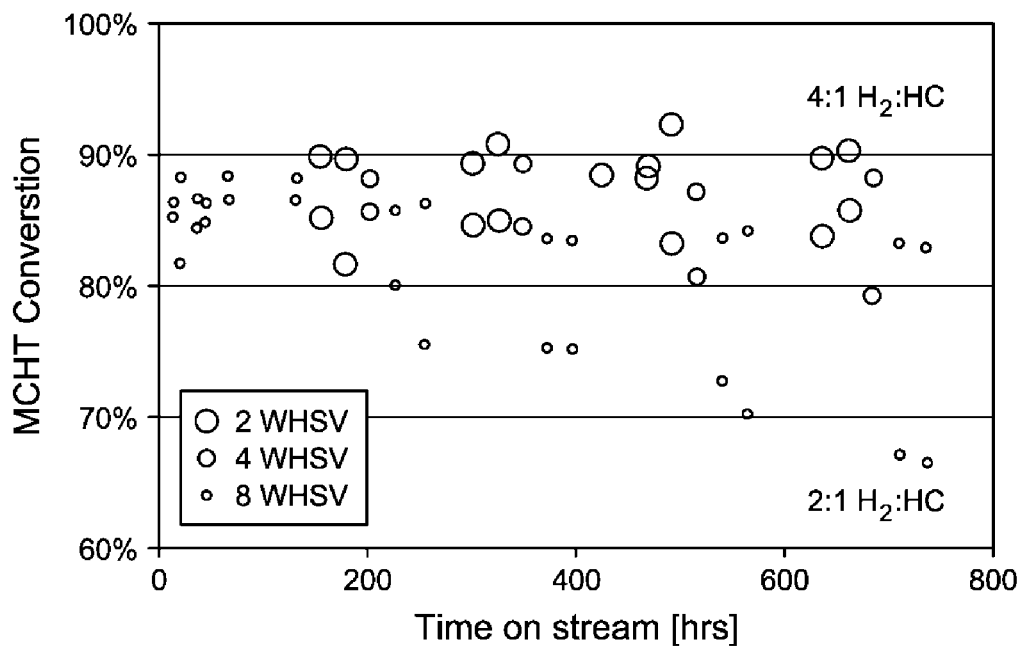
FIG. 1 is a graph of weight % conversion of methylcyclohexyltoluene (MCHT) against time on stream at a temperature of 430° C. and varying WHSV and $H_2$/HC values (molar) for the process of Example 4.

An improved process is described for activating and operating catalysts useful for the dehydrogenation of cyclohexylbenzene and/or alkyl-substituted cyclohexylbenzene compounds. As used herein, the term "alkyl-substituted cyclohexylbenzene" is intended to include cyclohexylbenzene compounds having one or more alkyl substituents on either the cyclohexane ring or the benzene ring or both. Thus, for example, suitable alkyl-substituted cyclohexylbenzene compounds for use in the present process include methylcyclohexylbenzene, cyclohexyltoluene, (methylcyclohexyl)toluene and dimethylcyclohexylxylenes. As will be discussed in more detail below such compounds can be produced by hydroalkylation of one or more of benzene, toluene and xylenes, including combinations of such $C_6$-$C_8$ aromatics, as well as by certain transalkylation reactions.

Dehydrogenation Catalyst

A suitable dehydrogenation catalyst for use in the present process comprises one or more elements or compounds thereof selected from Group 10 of the Periodic Table of Elements, for example nickel, palladium, platinum, preferably platinum, on a refractory support. In one embodiment, the Group 10 element is present in an amount from 0.1 to 5 wt % of the catalyst. In some cases, the dehydrogenation catalyst may also include tin or a tin compound. In one embodiment, the tin is present in an amount from 0.1 to 5 wt %, such as from 0.05 to 2.5 wt %, of the catalyst.

As used herein, the numbering scheme for the Periodic Table Groups is the New notation as described in Chemical and Engineering News, 63(5), 27 (1985).

The support employed in the dehydrogenation catalyst is refractory in the sense that it is capable of withstanding the conditions employed in the dehydrogenation reaction without physical or chemical changes. Non-limiting examples of suitable refractory support materials include: alumina, silica, silica-alumina, titania, calcium oxide, strontium oxide, barium oxide, magnesium oxide, carbon, zirconia, diatomaceous earth, lanthanide oxides including cerium oxide, lanthanum oxide, neodynium oxide, yttrium oxide and praesodynium oxide, oxides of chromium, thorium, uranium, niobium and tantalum, tin oxide, zinc oxide, and aluminum phosphate.

In one embodiment, the refractory support is selected to have one or more, such as two or more, and desirably all, of the following acidic properties:
 (i) an alpha value between 0.1 to 10, preferably less than 1;
 (ii) a combined Bronsted and Lewis acid activity from 0.1 to 0.5 mmol/gm of the dehydrogenation catalyst, preferably about 0.1 mmol/gm; and
 (iii) a temperature programmed ammonia adsorption from 0.1 to 1 mmol/gm of the dehydrogenation catalyst, preferably about 0.1 mmol/gm.

Alpha value is a measure of the cracking activity of an acid catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, page 395.

The Bronsted and Lewis acid activities of an acidic material can be determined from the amount of pyridine adsorbed by the material. Such a test can be conducted by grinding the material to a size of less than 100 mesh and then pressing the ground material into a thin self-supporting wafer typically having a weight from 10~15 mg/cm$^2$. The wafer is then placed in an IR transmission cell equipped with CaF$_2$ windows and the wafer is pre-calcined in vacuum at 450° C. for 1.5 hr. The adsorption of pyridine is carried out at 250° C. from a glass vial attached to the manifold of the cell. The pyridine partial pressure is measured by a Baratron pressure transducer. The IR bands at 1545 cm$^{-1}$ and 1450 cm$^{-1}$ are used for the quantitative evaluation of Bronsted and Lewis acid sites, respectively. The amount of pyridium ions and Lewis-bonded pyridine per gram of sample can then be calculated using Beer-Lambert's law according to the formula:

$$n/m=(A_i*Q)/(\epsilon_i*m)$$

where $A_i$ is the integrated absorbance [cm$^{-1}$];
 $\epsilon_i$ is the integrated molar extinction coefficient [cm/μmol];
 m is the mass of wafer [g];
 Q is the geometric surface area of wafer [cm$^2$]; and
 n is the amount of pyridine [μmol].

Values for the integrated molar extinction coefficients were adopted from the literature [C. A. Emeis, J. Catal., 141 (1993) 347] to be $\epsilon_B$=1.67 cm/μmol for pyridium ions, and $\epsilon_L$=2.22 cm/μmol for Lewis-bonded pyridine.

The temperature programmed ammonia absorption (TPAA) measures the total number of acid sites in a sample via the formation of an adsorption complex with Bronsted and Lewis acid sites. In the tests cited herein, before the ammonia absorption, each sample was calcined in air at 500° C. for 1 hr to remove any absorbed moisture and volatiles. The sample was cooled down in air to 250° C. Then the system was switched to a helium stream. Recurrent pulses of 1% NH$_3$/He were added into the system. The sample with ammonia absorption was weighed in-situ by the microbalance to determine the TPAA value in mmol of NH$_3$/gm of the sample. After sample acid sites were saturated with NH$_3$, the system was purged with helium stream to remove physical absorbed ammonia. The system was ramped from 250° C. to 500° C. with a ramping rate of 5° C./min to generate a programmed ammonia desorption (TPAD) profile.

Suitable refractory acidic supports for the dehydrogenation catalyst comprise one or more supports selected from the group consisting of alumina, silica, silica-alumina, titania, calcium oxide, strontium oxide, barium oxide, magnesium oxide, carbon, zirconia, diatomaceous earth, lanthanide oxides including cerium oxide, lanthanum oxide, neodynium oxide, yttrium oxide and praesodynium oxide, oxides of chromium, thorium, uranium, niobium and tantalum, tin oxide, zinc oxide, and aluminum phosphate. A preferred support is alumina.

Preparation and Activation of the Dehydrogenation Catalyst

The dehydrogenation catalyst can be produced by any known method of adding a Group 10 metal compound and, where applicable, a tin compound to a refractory support. For example, suitable methods include impregnation, ion exchange and precipitation. In particular, where the dehydrogenation catalyst contains tin, the catalyst may be prepared by impregnating the support with an aqueous solution of a suitable tin compound, such as tin chloride, and/or tin tartrate. The impregnated support containing Sn is then dried in air, such as at 120° C. for 4 hrs and, and may then be calcined, such as at 538° C. in air for 3 hrs, to convert the tin to an oxide form. Afterwards, Pt may be added to the Sn-containing support by impregnation with an aqueous solution of a suitable platinum compound, such as (NH$_3$)$_4$Pt(NO$_3$)$_2$. The sample containing Sn and Pt is dried in air, such as at 120° C. for 4 hrs, and then calcined, such as at 360° C. in air for 3 hrs. Alternatively, the order of impregnation can be reversed (Pt added before the Sn) and a single calcination can be used after addition of both metals.

Generally, the resultant catalyst contains the Group 10 metal and, where applicable, tin in an oxidized state and so, before use of the catalyst in the dehydrogenation of cyclohexylbenzene and/or alkyl-substituted cyclohexylbenzene compounds, it is desirable to activate the catalyst to convert the Group 10 metal and/or tin to a reduced form, and generally a zerovalent form. According to the present process, such activation is effected by heating the catalyst, either as-calcined or after an initial drying step, in the presence of hydrogen from a first temperature to a second, higher temperature at a ramp rate no more than 100° C./hour, such as no more than 50° C./hour, for example no more than 20° C./hour. In terms of ranges, the ramp rate for the heating from the first to the second temperature may be from 0.5° C. to 100° C./hour, such as from 0.5° C. to 50° C./hour, for example from 1° C. to 20° C./hour. Preferably the second higher temperature is at least 100° C. higher than the first temperature, preferably at least 150° C. higher, preferably at least 200° C. higher. The catalyst is then reacted with hydrogen at the second temperature for a time from 3 to 300 hours, such as from 30 to 150 hours, for example from 40 to 80 hours, sufficient to achieve the required activation.

In some embodiments, the first temperature in the above activation process is from 0° C. to 200° C. Where the activation is conducted without an initial drying step, the first temperature may be at or near ambient temperature, for example, from 0° C. to 40° C., such as from 10° C. to 30°

C. Where the activation is conducted after an initial drying step, the first temperature may be at or near the drying temperature, such as from 60° C. to 200° C., for example from 120° C. to 150° C.

In some embodiments, the second temperature in the above activation process is from 60° C. to 500° C. Preferred values for the second temperature are from 120° C. to 450° C., for example from 200° C. to 430° C. The second temperature may be held substantially constant during the activation process or can be varied within the above ranges.

Hydrogen is supplied to the catalyst during the activation process, that is both during ramping from the first to second temperature and during heating at the second temperature. Hydrogen may also be supplied to the catalyst during any initial drying process. A suitable hydrogen flow rate for the supply of hydrogen during heating at the second temperature is from 10 to 300 sccm/g of catalyst, for example from 100 to 150 sccm/g of catalyst. Similar supply rates apply to the hydrogen fed to the catalyst during the ramping step and the optional drying step.

The activation process can be conducted in any known form of reactor, such as a fixed bed reactor, a moving bed reactor or a fluidized bed reactor. Preferably, the activation process is conducted in-situ in the reactor used in the subsequent dehydrogenation process.

Dehydrogenation Process

The activated catalyst produced by the present process is found to exhibit excellent activity and stability when used in the dehydrogenation of feeds comprising cyclohexylbenzene and/or alkyl-substituted cyclohexylbenzene compounds. Suitable conditions for the dehydrogenation reaction include a temperature from 200° C. to about 600° C. and a pressure from 100 kPa-a to 3550 kPa-a, such as a temperature from 200° C. to 500° C. and a pressure from 100 kPa to 1600 kPa-a, for example a temperature from 350° C. to about 450° C. and a pressure from 340 kPa-a to about 1400 kPa-a. The dehydrogenation reaction may be conducted in the presence of hydrogen such that the hydrogen to hydrocarbon molar ratio in the dicyclohexylbenzene compounds feed is in excess of 2, preferably at least 4.

In some embodiments, it may be desirable to ensure that the dehydrogenation feed comprises less than 0.1 wt % of dicyclohexylbenzene compounds, such as may be present where the feed comprises the effluent from a hydroalkylation process. In such a case, the hydroalkylation effluent may undergo a distillation process to reduce the level of dicyclohexylbenzene compounds to the desired value before the effluent is supplied to the dehydrogenation reaction.

The dehydrogenation process can be conducted in any known form of reactor, such as a fixed bed reactor, a moving bed reactor, a fluidized bed reactor or a distillation reactor.

Dehydrogenation Feeds

The activated catalyst produced by the present process can be used in the dehydrogenation of a wide variety of feeds comprising cyclohexylbenzene and/or alkyl-substituted cyclohexylbenzene compounds, especially those obtained by the hydroalkylation of benzene, toluene and/or xylenes. For example, when contacted with a suitable bifunctional catalyst (discussed below) under hydroalkylation conditions, benzene initially undergoes partial hydrogenation to cyclohexene which then alkylates additional benzene to produce cyclohexylbenzene. The overall reaction can be summarized as follows:

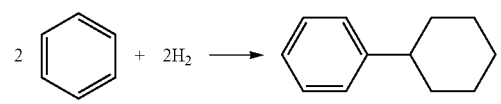

Similarly, in the case of toluene, hydroalkylation yields a mixture of (methylcyclohexyl)toluene isomers according to the reaction:

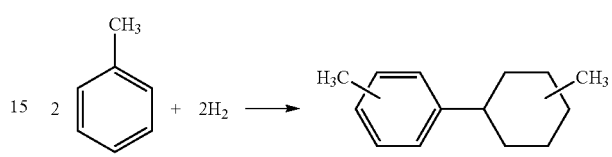

whereas with xylenes the hydroalkylation produces a mixture of dimethylcyclohexylxylenes according to the reaction:

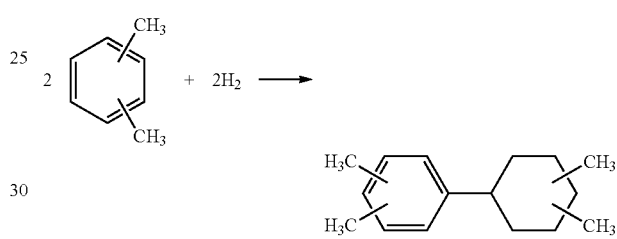

Suitable dehydrogenation feeds can also be produced by hydroalkylation of a mixture of two or more of benzene, toluene and/or xylenes. For example, hydroalkylation of a mixture of benzene and toluene produces methylcyclohexylbenzenes and/or cyclohexyltoluenes, in addition to cyclohexylbenzene and (methylcyclohexyl)toluenes.

Suitable bifunctional catalysts for use in the above hydroalkylation reactions comprise a hydrogenation component and a solid acid alkylation component, typically a molecular sieve. The catalyst may also include a binder such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the catalyst, although suitable metals include palladium, ruthenium, nickel, zinc, tin, and cobalt, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069 and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:
  molecular sieves made from a common first degree crystalline building block unit cell, which unit cell has the MWW framework topology (a unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
  molecular sieves made from a common second degree building block, being a 2-dimensional tiling of such MWW framework topology unit cells, forming a monolayer of one unit cell thickness, preferably one c-unit cell thickness;
  molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
  molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof Related zeolite UZM-8 is also suitable for use as the hydroalkylation catalyst.

In addition to the benzene, toluene and/or xylene and hydrogen, a diluent, which is substantially inert under hydroalkylation conditions, may be supplied to the hydroalkylation reaction. In certain embodiments, the diluent is a hydrocarbon, in which the desired cycloalkylaromatic product is soluble, such as a straight chain paraffinic hydrocarbon, a branched chain paraffinic hydrocarbon, and/or a cyclic paraffinic hydrocarbon. Examples of suitable diluents are decane and cyclohexane. Although the amount of diluent is not narrowly defined, desirably the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

Although the hydroalkylation reaction is highly selective towards the desired cyclohexylbenzene compounds, the effluent from the hydroalkylation reaction may contain some unreacted benzene, toluene and/or xylene as well as fully saturated and dialkylated by-products. The unreacted aromatic compounds may be recovered by distillation and recycled to the reactor. The remaining effluent from such distillation may be further distilled to separate the monoalkylated products from the dialkylated by-products and other heavies. However, depending on the level of conversion in the hydroalkylation reaction and the amount, if any, of separation of the hydroalkylation effluent, the feed to the present dehydrogenation process may comprise large quantities of the unreacted aromatic starting materials and their fully saturated analogs. For example, where the dehydrogenation feed is produced by hydroalkylation of benzene, the feed may also contain up to 90 wt % benzene and/or cyclohexane. Similarly, where the dehydrogenation feed is produced by hydroalkylation of an alkylated benzene, such as toluene, the feed may also contain up to 90 wt % of the alkylated benzene, such as toluene, and/or the corresponding alkylated cyclohexane, such as methylcyclohexane.

In another embodiment, the dehydrogenation feed may comprise methylcyclohexylbenzene and/or cyclohexyltoluene produced by the transalkylation of cyclohexylbenzene with toluene. Thus, as discussed above, the production of methylbiphenyl compounds from benzene by hydroalkylation/dehydrogenation requires the addition of methyl group(s) to the biphenyl product of the dehydrogenation stage. This would normally be achieved by alkylation with methanol. However, an attractive alternative route involves transalkylation of cyclohexylbenzene product of the hydroalkylation step with toluene. Such a transalkylation reaction can be conducted in the presence of a solid acid catalyst, such as a molecular sieve and in particular a large pore molecular sieve having a Constraint Index (as defined in U.S. Pat. No. 4,016,218) less than 2 and/or a molecular sieve of the MCM-22 family. Suitable conditions for the transalkylation reaction include a temperature from 75° C. to 250° C., such as from 100° C. to 200° C., for example 125° C. to 160° C. and a pressure from 100 to 3550 kPa-absolute, such as from 1000 to 1500 kPa-absolute. In some embodiments, the transalkylation reaction may be conducted in the same reactor as the hydroalkylation reaction.

In another embodiment, this invention relates to:
1. A process for dehydrogenating cyclohexylbenzene and/or alkyl-substituted cyclohexylbenzene compounds, the process comprising:
(a) providing a dehydrogenation catalyst comprising at least one Group 10 metal compound on a support;
(b) heating the dehydrogenation catalyst in the presence of hydrogen from a first temperature from 0° C. to 200° C. to a second, higher temperature from 60° C. to 500° C. at a ramp rate no more than 100° C./hour;
(c) contacting the dehydrogenation catalyst with hydrogen at the second temperature for a time from 3 to 300 hours to produce an activated dehydrogenation catalyst; and
(d) contacting a feed comprising cyclohexylbenzene and/or an alkyl-substituted cyclohexylbenzene compound with hydrogen in the presence of the activated dehydrogenation catalyst under conditions effective to produce a dehydrogenation reaction product comprising biphenyl and/or an alkyl-substituted biphenyl compound.
2. The process of paragraph 1, wherein the at least one Group 10 metal comprises platinum.
3. The process of paragraph 2, wherein the dehydrogenation catalyst comprises from 0.1 to 5% wt % of elemental platinum.
4. The process of any of paragraphs 1 to 3, wherein the dehydrogenation catalyst further comprises a tin compound, preferably tin chloride or tin tartrate.
5. The process of paragraph 4, wherein the dehydrogenation catalyst comprises from 0.1 to 5 wt % of elemental tin.
6. The process of any of paragraphs 1 to 5 and further comprising:
(e) treating a support with a solution containing a Group 10 metal compound in a solvent; and
(f) removing the solvent from the treated support to produce the dehydrogenation catalyst on a support provided in (a).
7. The process of any of paragraphs 1 to 6, wherein the temperature ramp during the heating (b) is from 0.5° C./hour to 100° C./hour.
8. The process of any of paragraphs 1 to 7, wherein the temperature ramp during the heating (b) is from 0.5° C./hour to 50° C./hour.
9. The process of any of paragraphs 1 to 8, wherein the temperature ramp during the heating (b) is from 1° C./hour to 20° C./hour.
10. The process of any of paragraphs 1 to 9, wherein hydrogen is supplied to the dehydrogenation catalyst at least during the contacting (c) at a rate of 10 to 300 sccm/g of catalyst.
11. The process of any of paragraphs 1 to 10, wherein the conditions in the contacting (d) include a hydrogen to hydrocarbon molar ratio in excess of 2, preferably at least 4.
12. The process of any of paragraphs 1 to 11, wherein the conditions in the contacting (d) include a temperature from 200° C. to 500° C. and a pressure from 100 kPa to 1600 kPa-a.
13. The process of any of paragraphs 1 to 12, wherein the feed comprises less than 0.1 wt % of dicyclohexylbenzene compounds.
14. The process of any of paragraphs 1 to 13, wherein the feed comprises cyclohexylbenzene produced by the hydroalkylation of benzene.
15. The process of any of paragraphs 1 to 14, wherein the feed comprises (methylcyclohexyl)toluene produced by the hydroalkylation of toluene.
16. The process of any of paragraphs 1 to 15, wherein the feed comprises dimethylcyclohexylxylenes from the hydroalkylation of xylenes.
17. The process of any of paragraphs 1 to 16, wherein the feed comprises methylcyclohexylbenzene and/or cyclohexyltoluene produced from the hydroalkylation of toluene and benzene or the transalkylation of cyclohexylbenzene with toluene.
18. The process of any of paragraphs 1 to 17, wherein the reactor feed also contains up to 90 wt % benzene or cyclohexane.
19. The process of any of paragraphs 1 to 17, wherein the reactor feed also contains up to 90 wt % alkylated benzene or alkylated cyclohexane.
20. The process of any of paragraphs 1 to 17, wherein the reactor feed also contains up to 90 wt % toluene and/or methylcyclohexane.
21. The process of any of paragraphs 1 to 20, wherein the first temperature is at least 100° C. higher than the second temperature in (b).
22. The process of any of paragraphs 1 to 21, wherein the support is selected from the group consisting of alumina, silica, silica-alumina, titania, calcium oxide, strontium oxide, barium oxide, magnesium oxide, carbon, zirconia, diatomaceous earth, lanthanide oxides including cerium oxide, lanthanum oxide, neodynium oxide, yttrium oxide and praesodynium oxide, oxides of chromium, thorium, uranium, niobium and tantalum, tin oxide, zinc oxide, and aluminum phosphate.
23. The process of any of paragraphs 1 to 22, wherein the feed of (d) comprises less than 0.1 wt % of dicyclohexylbenzene.
24. The process of any of paragraphs 1 to 22, wherein the temperature ramp rate of (b) is 0.5 to 100° C./hour, alternately 0.5 to 50° C./hour, alternately 1 to 20° C./hour.

EXPERIMENTAL

The invention will now be more particularly described with reference to the accompanying drawings and the following non-limiting Examples. Unless otherwise indicated, room or ambient temperature is about 23° C.

Example 1

Preparation of 0.3%Pd/MCM-49 Hydroalkylation Catalyst 80 parts MCM-49 zeolite crystals are combined with 20 parts pseudoboehmite alumina on a calcined dry weight basis. The MCM-49 and pseudoboehmite alumina dry powder is placed in a muller or a mixer and mixed for about 10 to 30 minutes. Sufficient water and 0.05% polyvinyl alcohol is added to the MCM-49 and alumina during the mixing process to produce an extrudable paste. The extrudable paste is formed into a ¹⁄₂₀ inch diameter quadralobe extrudate using an extruder. After extrusion, the quadralobe extrudate is dried at a temperature ranging from 250° F. to 325° F. (121 to 163° C.). After drying, the dried extrudate is heated to 1000° F. (538° C.) under flowing nitrogen. The extrudate is then cooled to ambient temperature and humidified with saturated air or steam.

After the humidification, the extrudate is ion exchanged with 0.5 to 1 N ammonium nitrate solution. The ammonium nitrate solution ion exchange is repeated. The ammonium nitrate exchanged extrudate is then washed with deionized water to remove residual nitrate prior to calcination in air. After washing the wet extrudate is dried. The exchanged and dried extrudate is next calcined in a nitrogen/air mixture to a temperature 1000° F. (538° C.). Afterwards, the calcined extrudate is cooled to room temperature. The 80% MCM-49, 20% $Al_2O_3$ extrudate was incipient wetness impregnated with a palladium (II) chloride solution (target: 0.30% Pd) and then dried overnight at 121° C. The dried catalyst was calcined in air at the following conditions: 5 volumes air per volume catalyst per minute, ramp from ambient to 538° C. at 1° C./min and hold for 3 hours.

Example 2

Hydroalkylation of Toluene

The catalyst of Example 1 was then tested in the hydroalkylation of a toluene feed using the reactor and process described below.

The reactor comprised a stainless steel tube having an outside diameter of: ⅜ inch (0.95 cm), a length of 20.5 inch (52 cm) and a wall thickness of 0.35 inch (0.9 cm). A piece of stainless steel tubing having a length of 8¾ inch (22 cm) and an outside diameter of ⅜ inch (0.95 cm) and a similar length of ¼ inch (0.6 cm) tubing were used in the bottom of the reactor (one inside of the other) as a spacer to position and support the catalyst in the isothermal zone of the furnace. A ¼ inch (0.6 cm) plug of glass wool was placed on top of the spacer to keep the catalyst in place. A ⅛ inch (0.3 cm) stainless steel thermo-well was placed in the catalyst bed to monitor temperature throughout the catalyst bed using a movable thermocouple.

1 gm of the catalyst was sized to 20/40 sieve mesh or cut to 1:1 length to diameter ratio, dispersed with quartz chips (20/40 mesh) then loaded into the reactor from the top to a volume of 5.5 cc. The catalyst bed typically was 15 cm. in length. The remaining void space at the top of the reactor was filled with quartz chips, with a ¼ plug of glass wool placed on top of the catalyst bed being used to separate quartz chips from the catalyst. The reactor was installed in a furnace with the catalyst bed in the middle of the furnace at a pre-marked isothermal zone. The reactor was then pressure and leak tested typically at 300 psig (2170 kPa).

The catalyst was pre-conditioned in situ by heating from 25° C. to 240° C. with $H_2$ flow at 100 cc/min and holding for 12 hours. A 500 cc ISCO syringe pump was used to introduce toluene feed to the reactor. The feed was pumped through a vaporizer before flowing through heated lines to the reactor. A Brooks mass flow controller was used to set the hydrogen flow rate. A Grove Mity Mite™ back pressure controller was used to control the reactor pressure typically at 150 psig (1135 kPa). GC analyses were taken to verify feed composition. The feed was then pumped through the catalyst bed held at the reaction temperature of 120° C. to 180° C. at a WHSV of 2 and a pressure of 15-200 psig (204-1480 kPa). The liquid products exiting the reactor flowed through heated lines routed to two collection pots in series, the first pot being heated to 60° C. and the second pot cooled with chilled coolant to about 10° C. Material balances were taken at 12 to 24 hrs intervals. Samples were taken and diluted with 50% ethanol for analysis. An Agilent™ 6890 gas chromatograph with FID detector was used for the analysis. The non-condensable gas products were routed to an on-line Hewlett Packard™ 5890 GC.

The major components of the hydroalkylation reaction effluent were toluene (66 wt %), (methylcyclohexyl)toluene (24 wt %), methylcyclohexane (9 wt %) and dialkylate (0.5 wt %).

Example 3

Preparation of 1% Pt/0.15% $Sn/SiO_2$ Dehydrogenation Catalyst

A 1% Pt/0.15% $Sn/SiO_2$ dehydrogenation catalyst was prepared by incipient wetness impregnation. A ¹⁄₂₀" quadralobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. The resultant product was calcined in air at 350° C. for 3 hours before being used in subsequent catalyst testing.

Example 4

Activation and Use of Dehydrogenation Catalyst of Example 3

The catalyst of Example 3 was used to dehydrogenate the hydroalkylation reaction effluent of Example 2 using the reactor and process described below.

The catalyst extrudate was crushed to 20/40 mesh and loaded into 9 mm diameter quartz tube reactors in quantities ranging from 0.25-1 g (to vary the corresponding weight based space velocity) after being diluted up to 4 g in crushed quartz. A quartz wool plug was used at the top and bottom of the catalyst bed to keep catalyst in place. 2 sets of 4 parallel reactors were placed in heated furnaces to control isothermal reaction temperature. Each reactor contained an internal thermocouple in the catalyst bed in a ⅛" thermowell. The reactors were topped off with the same quartz chips.

The catalyst in all reactors was activated in situ by the following procedure. The reactor was purged with $H_2$ for 30 minutes. Then the temperature was ramped at 9° F. (5° C.)/hr. to 248° F. (120° C.) and then held at 248° F. (120° C.) for 1 hr to dry the catalyst. Hydrogen flow was set to 56 cc/min, the pressure was adjusted to 50 psig (446 kPa-a) and the temperature was ramped at 9° F. (5° C.)/hr. to 842° F. (450° C.). The temperature was held at 842° F. (450° C.) for 12 hours. At the end of 12 hrs, the temperature was ramped down at 9° F. (5° C.)/hr. to the desired dehydrogenation temperature. The pressure was then increased to 100 psig (791 kPa-a). Feed was introduced at these conditions via ISCO pumps.

Figure 2:
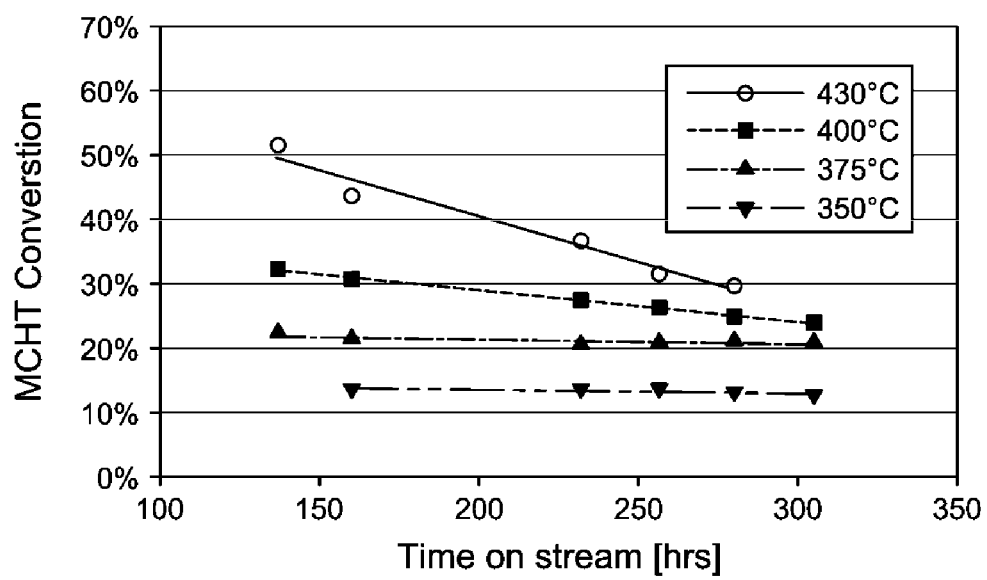
FIG. 2 is a graph of weight % conversion of methylcyclohexyltoluene (MCHT) against time on stream at a WHSV of 16 and $H_2$/HC of 4 (molar) and varying temperatures (in ascending order of 350° C., 375° C., 400° C., and 430° C.) for the process of Example 4.

The feed was pumped through a vaporizer before being mixed in-line with $H_2$ at a 2:1 to 4:1 molar ratio of $H_2$ to liquid feed. The feed was then pumped through the catalyst bed held at the reaction temperature of between 350° C. and 450° C. WHSV was varied between 2 and 16. The products exiting the reactor were condensed and collected in intervals (approximately one sample per day per reactor) and analyzed by GC. The results are shown in FIGS. 1 and 2. In particular, it will be seen that, by increasing the $H_2$:hydrocarbon molar feed ratio from 2 to 4, the catalyst activity (measured by MCHT conversion) remained higher over a longer period of time (FIG. 1). Specifically, at a temperature of 400° C. and 8 WHSV, MCHT conversion at 730 hours on stream is greater than 80% in the case of $H_2$:hydrocarbon=4. In the case of $H_2$:hydrocarbon=2, the conversion is less than 70%. Further, at WHSV=16, the conversion of MCHT declines more rapidly at higher temperatures (FIG. 2).

Example 5

Alternative Activation Process for Dehydrogenation Catalyst of Example 3

The dehydrogenation process of Example 4 was repeated but with the catalyst being initially activated in situ by heating from room temperature to 430° C. with $H_2$ flow at 100 cc/min, at a temperature ramping rate of 2° C./min and 100 psig (791 kPa-a) pressure.

Figure 3:
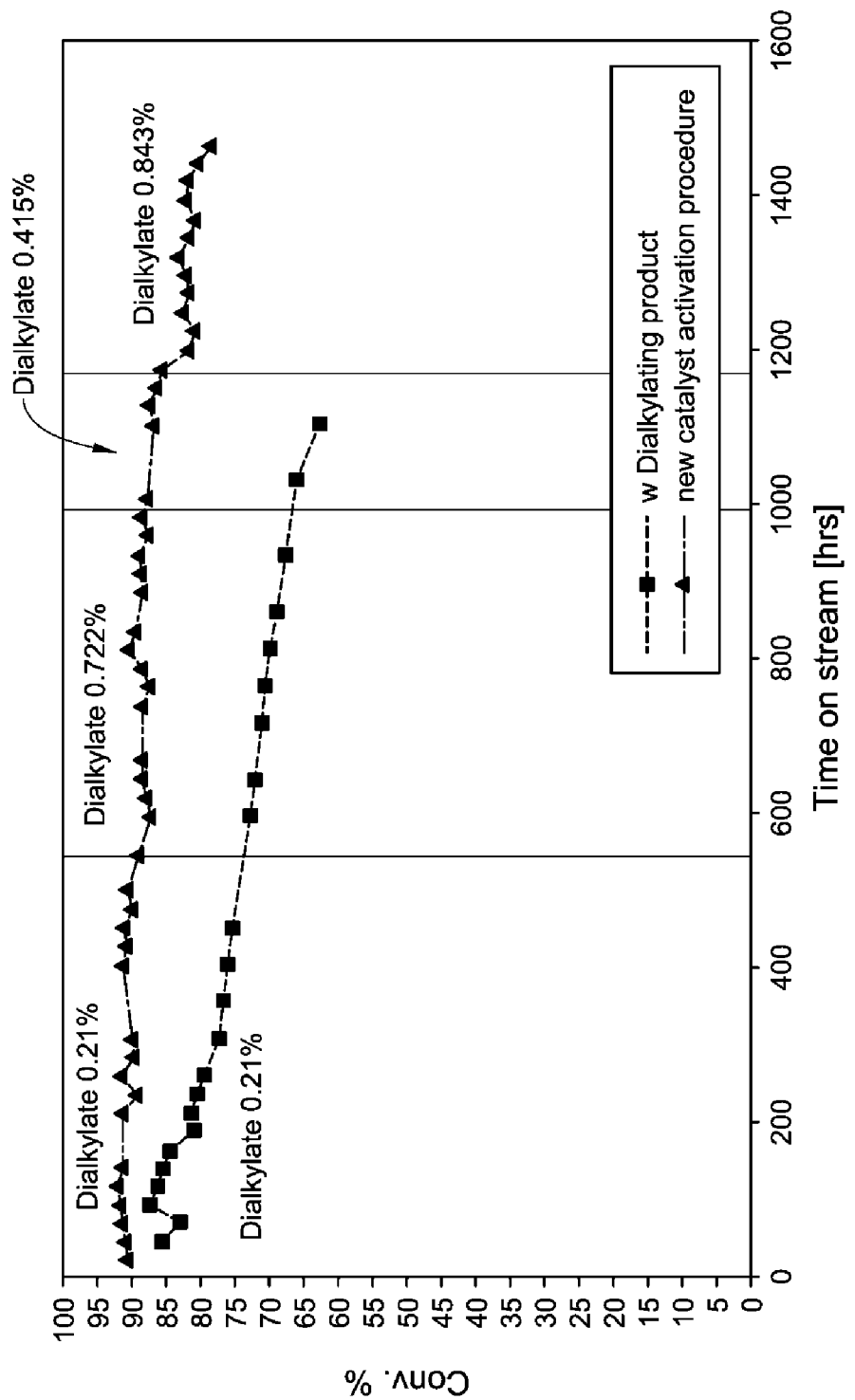
FIG. 3 is a graph comparing weight % conversion of the dehydrogenation feed against time on stream at a temperature of 430° C., a pressure of 100 psig (791 kPa-a), WHSV of 2 and $H_2$/HC of 2:1 (molar) for the processes of Examples 4 and 5.

The results of the dehydrogenation processes of Examples 4 and 5 at a temperature of 430° C., WHSV of 2 and $H_2$/HC of 2:1 (molar) are compared in FIG. 3. In the case of the process of Example 4, the amount of dialkylate in the feed was varied during the test from 0.21 wt % for the first 550 hours, to 0.722 wt % for the next 450 hours, to 0.415 wt % for the next 175 hours, and to 0.843 wt % for the final 325 hours (for a total of about 1500 hours from the beginning of the test). In the case of the process of Example 4, the amount of dialkylate in the feed was maintained at 0.21 wt % throughout the duration of the test. It will be seen that, with the activation procedure of Example 4, it was possible to run the reaction for more than 1500 hrs with only limited catalyst deactivation. In contrast, the catalyst produced by the procedure of Example 5 deactivated more rapidly, even though the dialkylate content of the feed was always at or below the level in Example 4.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law and whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A process for dehydrogenating cyclohexylbenzene and/or alkyl-substituted cyclohexylbenzene compounds, the process comprising:
    (a) providing a dehydrogenation catalyst comprising at least one Group 10 metal compound on a support;
    (b) heating the dehydrogenation catalyst in the presence of hydrogen from a first temperature from 0° C. to 200° C. to a second, higher temperature from 60° C. to 500° C. at a ramp rate of no more than 100° C./hour;
    (c) contacting the dehydrogenation catalyst with hydrogen at the second temperature for a time from 3 to 300 hours to produce an activated dehydrogenation catalyst; and
    (d) contacting a feed comprising cyclohexylbenzene and/or an alkyl-substituted cyclohexylbenzene compound with hydrogen in the presence of the activated dehydrogenation catalyst under conditions effective to produce a dehydrogenation reaction product comprising biphenyl and/or an alkyl-substituted biphenyl compound.

2. The process of claim 1, wherein the at least one Group 10 metal comprises platinum.

3. The process of claim 1, wherein the dehydrogenation catalyst comprises from 0.1 to 5wt % of elemental platinum.

4. The process of claim 1, wherein the dehydrogenation catalyst further comprises a tin compound.

5. The process of claim 4, wherein the tin compound comprises tin chloride or tin tartrate.

6. The process of claim 1, wherein the dehydrogenation catalyst comprises from 0.1 to 5 wt % of elemental tin.

7. The process of claim 1 further comprising the following steps prior to the providing (a):
    (i) treating the support with a solution containing the Group 10 metal compound in a solvent; and
    (ii) removing the solvent from the treated support to produce the hydrogenation catalyst on the support provided in (a).

8. The process of claim 1, wherein the ramp rate during the heating (b) is from 0.5° C./hour to 100° C./hour.

9. The process of claim 1, wherein the ramp rate during the heating (b) is from 0.5° C./hour to 50° C./hour.

10. The process of claim 1, wherein the ramp rate during the heating (b) is from 1° C./hour to 20° C./hour.

11. The process of claim 1, wherein hydrogen is supplied to the dehydrogenation catalyst at least during the contacting (c) at a rate of 10 to 300 sccm/g of catalyst.

12. The process of claim 1, wherein the conditions in the contacting (d) include a hydrogen to hydrocarbon molar ratio in excess of 2.

13. The process of claim 1, wherein the conditions in the contacting (d) include a temperature from 200° C. to 500° C. and a pressure from 100 kPa to 1600 kPa-a.

14. The process of claim 1, wherein the feed comprises less than 0.1 wt % of dicyclohexylbenzene compounds.

15. The process of claim 1, wherein the feed comprises cyclohexylbenzene produced by the hydroalkylation of benzene.

16. The process of claim 1, wherein the feed comprises (methylcyclohexyl)toluene produced by the hydroalkylation of toluene.

17. The process of claim 1, wherein the feed comprises dimethylcyclohexylxylenes from the hydroalkylation of xylenes.

18. The process of claim 1, wherein the feed comprises methylcyclohexylbenzene and/or cyclohexyltoluene produced from the hydroalkylation of toluene and benzene or the transalkylation of cyclohexylbenzene with toluene.

19. The process of claim 1, wherein the feed also contains up to 90 wt % benzene or cyclohexane.

20. The process of claim 1, wherein the feed also contains up to 90 wt % alkylated benzene or alkylated cyclohexane.

21. The process of claim 1, wherein the feed also contains up to 90 wt % toluene and/or methylcyclohexane.

22. The process of claim 1, wherein the second temperature is at least 100° C. higher than the first temperature in (b).

23. The process of claim 1, wherein the support is selected from the group consisting of alumina, silica, silica-alumina, titania, calcium oxide, strontium oxide, barium oxide, magnesium oxide, carbon, zirconia, diatomaceous earth, lanthanide oxides including cerium oxide, lanthanum oxide, neodynium oxide, yttrium oxide and praesodynium oxide, oxides of chromium, thorium, uranium, niobium and tantalum, tin oxide, zinc oxide, and aluminum phosphate.

24. The process of claim 1, wherein the conditions in the contacting (d) include a hydrogen to hydrocarbon molar ratio of at least 4.

25. The process of claim 1, wherein the feed of (d) comprises less than 0.1 wt % of dicyclohexylbenzene.

* * * * *